Figure 1:
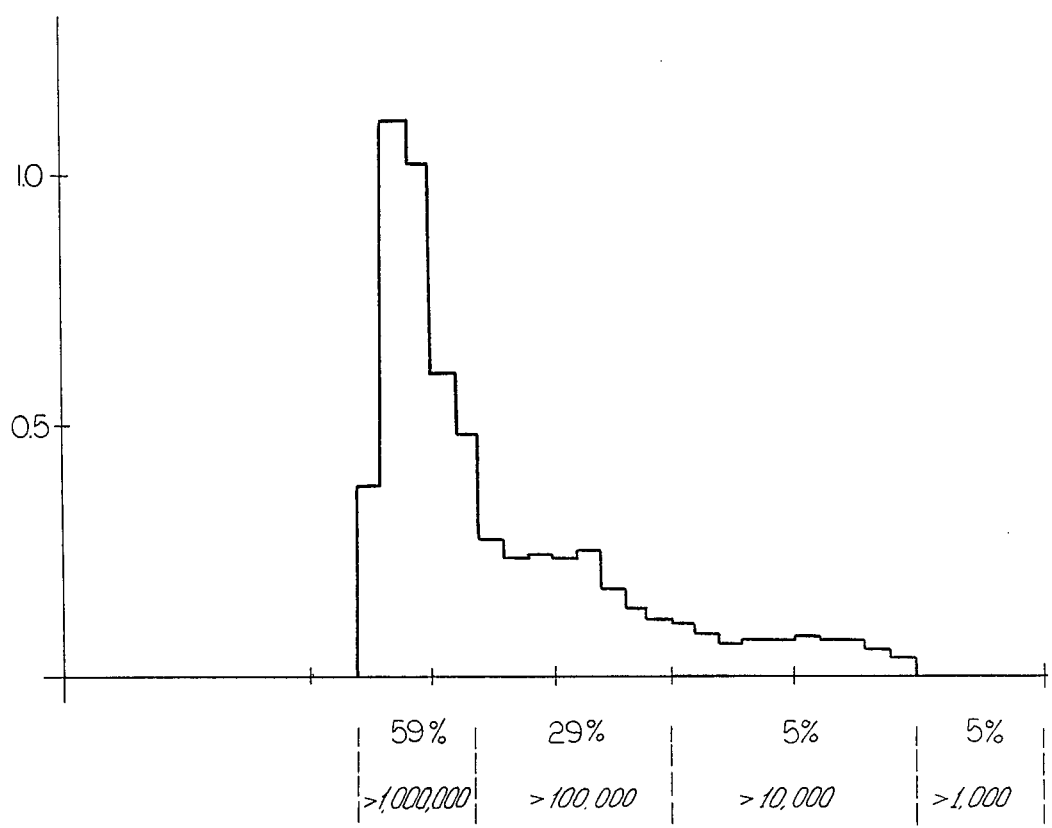

United States Patent [19]

Emoëdi

[11] Patent Number: 4,855,284

[45] Date of Patent: Aug. 8, 1989

[54] CALCIUM AND MAGNESIUM COMPLEXES OF PHYTOHEMAGGLUTININ-POLYHETEROGLYCANS, THEIR PREPARATION AND PHARMACEUTICAL FORMULATIONS

[75] Inventor: Gabriel Emoëdi, Basel, Switzerland

[73] Assignee: Intex Pharmazeutische Produkte AG, Basel, Switzerland

[21] Appl. No.: 897,713

[22] Filed: Aug. 18, 1986

[30] Foreign Application Priority Data

Aug. 23, 1985 [CH] Switzerland ............ 3651/85

[51] Int. Cl.$^4$ ........................... C07K 15/14
[52] U.S. Cl. ........................... 514/8; 514/2; 530/370; 530/372; 530/375; 530/379; 530/395; 530/396
[58] Field of Search ............ 530/370, 372, 375, 379, 530/396, 395; 514/2, 8

[56] References Cited

U.S. PATENT DOCUMENTS

| | | | |
|---|---|---|---|
| 3,432,489 | 3/1969 | Nitta et al. | 424/180 X |
| 4,225,486 | 9/1980 | Suzuki | 530/379 X |
| 4,751,218 | 6/1988 | Smets et al. | 514/8 X |

FOREIGN PATENT DOCUMENTS

| | | |
|---|---|---|
| 089529 | 9/1983 | European Pat. Off. |
| 3042491 | 7/1982 | Fed. Rep. of Germany |
| 7310979 | 6/1979 | Japan |
| 105533 | 6/1982 | Japan |

OTHER PUBLICATIONS

Chem. Pharm. Bull. 29 (1981) 2277-2282.
Chem Abstract-97 (1982) 44198 C 1981.
The Merck Index 1983, 1273.
Chem Abstract 97 (1982) 742815, 1982.
Ullmans Encyclopedia of Industrial Chemistry, 5th Ed. vol. A3 (1985) cover page and p. 23.
Medical and Pharmaceutical Dictionary, 4th Ed. (1981) cover page and pp. 257-258.

Primary Examiner—Howard E. Schain
Attorney, Agent, or Firm—Ladas & Parry

[57] ABSTRACT

New calcium and magnesium complexes of phytohemagglutinin-polyheteroglycans are distinguished inter alia by cytoprotective, antiinflammatory and immunostimulating properties. They have characteristic molecular weights and distribution thereof, infrared spectra and compositions in respect of calcium and/or magnesium, phosphorus, glycans and amino acids. The preparation is carried out by extraction of the phytohemagglutinin-polyglycans with water of weakly alkaline pH from plants, in particular of the families Compositae, Malvaceae, Cucurbitaceae and Gramineae, and precipitation with an alcohol which is miscible with water. The complexes can be used for the treatment of ulcers, inflammations or viral infections, or as immunostimulant.

15 Claims, 2 Drawing Sheets

CALCIUM AND MAGNESIUM COMPLEXES OF PHYTOHEMAGGLUTININ-POLYHETEROGLYCANS, THEIR PREPARATION AND PHARMACEUTICAL FORMULATIONS

The present invention relates to new calcium and magnesium complexes of phytohemagglutinin-polyheteroglycans of plant origin, to a process for their preparation, and to pharmaceutical formulations which contain these complexes as active compound.

The essential constituents of the new complexes are thus (a) phytohemagglutinins, that is to say proteins of the lectin type, which, as a consequence of their belonging to this type, are able to form complexes with polyglycans, in the present case with (b) oligosaccharide polymers which principally contain galactose and glucose, and (c) calcium and/or magnesium ions.

Lectins of plant origin have been known for 100 years now. According to their definition, they are proteins which bind strongly to carbohydrate but do not exercise any enzymatic action. The name phytohemagglutinin indicates that most lectins are able to agglutinate erythrocytes [Literature survey in Advances in Carbohydrate Chemistry and Biochemistry 35, 127-149 (1978); Physiol. Plant. 49, 437-442 (1980); J. Biol. Chem. 256, 12905-12910 (1981)]. Among the diverse biological activities of the lectins, particularly noteworthy are their actions stimulating cell growth and cell multiplication. As polyclonal stimulators, they increase lymphocyte mytosis in humans and animals, mainly by stimulation of the T-cells. In vitro, this increase can be shown in the interferon production of human leucocytes.

The blastogenic activity of the lymphocytes in response to phytohemagglutinins is utilized in investigation of immunocompetence, thus, for example, in the diagnosis of malignant tumors [Bioscience 34, 95-98 (1984); Lancet 1978, 1275].

Divalent ions, in particular calcium ions, are necessary for the biological activity of the lectins [J. Mol. Biol. 32, 453 (1968)].

Finally, the antiinflammatory action of the lectins is also worth mentioning [Japan J. Pharmacol. 32, 139-142 (1982)].

However, apart from their advantageous biological properties, the said compounds also have disadvantageous actions; for example their are among the natural products lectins of extremely high toxicity, such as ricin (lectin from Ricinus communis), whose $LD_{50}$ in mammals is about 1 microgram/kg.

Apart from the proteins, materials forming other large macromolecules are the carbohydrates, namely oligosaccharides and polysaccharides which commonly occur in nature. The antiinflammatory action of the arabino-fucoglycan polymers is known from the literature [Chem. Pharm. Bull. 32, 1385-1391 (1984)].

An antiinflammatory action of mucilaginous substances of plant origin with a polyglycan component was also previously known, but hitherto no medicines have been produced from these substances.

It has now been found, surprisingly, that it is possible to prepare from particular plants or parts of plants new complexes which contain lectins, polyheteroglycans and calcium and/or magnesium ions and which are distinguished by remarkable cytoprotective, antiinflammatory, immunoregulating or immunostimulating, and antiviral actions, but without having the disadvantageous properties of the abovementioned macromolecules of biological origin. Viewed more precisely, these complexes contain about 3 to 25% phytohemagglutinins, about 40 to 60% polyheteroglycans and, after combustion, at least 15% inorganic substances, including, in particular, calcium and/or magnesium, which are necessary in the form of ions for the biological activity of the product.

The invention is described in detail hereinafter.

Suitable starting materials are, in particular, plants of the families Compositae, Malvaceae, Cucurbitaceae and Gramineae, for example Tussilago farfara, Althea officinalis, Cucurbita pepo convar. Styriaca and Triticum vulgare. Use is made of the appropriate plant parts after they have been sliced finely, comminuted or ground to a paste.

When fresh plant material is used, after or also during the comminution of the plant it is extracted with water of weakly alkaline pH, where appropriate with addition of methanol or ethanol or of a salt used for brining. It is advantageous to use for this purpose an approximately 0.8- to 1.0-fold volume of extraction medium, relative to the weight of the plant material used. The extraction medium is preferably composed of a buffer solution of pH about 8 to 9, or of water of weakly alkaline pH, containing about 10 to 20% by volume of methanol or ethanol, or of a weakly alkaline, aqueous solution of a salt such as sodium chloride, potassium chloride, ammonium chloride or calcium chloride, for example in a concentration of up to 0.2 mole/liter. In the case of the latter extraction medium, the increase in solubility of organic substances in water as a consequence of the brining effect is exploited. The addition of methanol or ethanol or of a salt to the extraction medium provides a product of higher purity.

When dried plant material is used, it is possible to use the same extraction media as described above, but they should be employed in far greater volume, for example in about 30- to 40-fold volume, relative to the weight of the plant material used.

The extraction can be carried out at room temperature, but gentle heating, for example up to about 40° C., can be advantageous in many cases. During the extraction, it is possible to employ kneading or slow stirring of the material, continuously or discontinuously.

In order to obtain a better yield, it is possible to repeat the extraction with the plant residue in the same way as already carried out. In this case, the individual extracts are combined for the subsequent processing.

After completion of the extraction, the aqueous or aqueous-alcoholic extract is removed from the remaining solid plant material by filtration of centrifugation.

The calcium and/or magnesium complex of the phytohemagglutinin-polyheteroglycans is then precipitated from the extract by treatment with a multiple of the volume of an alcohol which is miscible with water. A suitable alcohol of this type is, inter alia, methanol, ethanol, propanol, isopropanol or tert.-butanol; methanol or ethanol is preferred. The alcohol is expediently added in an amount such that the alcohol content of the solution reaches 75 to 95% by volume. This precipitation reaction is carried out at 20 to a maximum of 40° C., and is advantageously repeated in order thus to isolate a purer product. In general, the alcohol is added with stirring, and then the mixture is left to stand until a precipitate has formed, for example for 1 to 24 hours. Finally, the precipitate is removed from the liquid by filtration or centrifugation. Where appropriate, the resulting product can be washed several times with an alcohol which is the same as or similar to that used in the precipitation, and then dried in a stream of air or in vacuo, at a maximum of 40° C.

It is frequently expedient to purify the crude product further by dissolving it in water or in a weakly alkaline buffer solution, removing any insolubles from the solution, precipitating the complex out of the solution by addition of ammonium sulfate, and removing it from the liquid. The dissolution is preferably carried out in a phosphate buffer solution whose pH is about 8 to 9 and whose amount is 5- to 20-fold relative to the weight of the product, and with stirring. Thereafter, solid ammonium sulfate is added in an amount such that the concentration of the solution reaches 20 to 40% and the lectin-rich product precipitates out of the solution. After having been left to stand for 1 to 24 hours, it can be isolated by filtration or centrifugation. This further purification can also be carried out in such a way that, after the dissolution in the alkaline buffer solution, the pH is adjusted to below 7.0, expediently between 3 and 7, by addition of a suitable acid, and then the precipitation with ammonium sulfate is carried out.

The precipitation can also be carried out stepwise; this results in products of different lectin/polyglycan ratios. If desired, the precipitation can be accelerated by gentle heating, for example up to about 40° C. Where appropriate, the purification which has been described can be repeated and thus a product which is even richer in phytohemagglutinins can be obtained.

The resulting product contains calcium and/or magnesium ions, but the amount of these ions varies depending on the nature and quality of the starting material and the conditions used for the extraction and isolation.

It is possible according to the invention to adjust the calcium and/or magnesium content of the complex to the desired figure of about 2 to 10% by weight in a separate operation. Irrespective of whether the crude or a purified complex is used as starting material, it is first dissolved in weakly alkaline solution, and this solution is first dialyzed in a standard dialysis tube from Kalle (manufacturer: Kalle AG, 6200 Wiesbaden-Biebrich, FRG) against demineralized water namely until its content of inorganic salts—measured by its residue on ignition—falls below 5%. The dialysis is, as a rule, carried out at room temperature, against running water, for example for 10 to 48 hours. The outside liquid is then replaced by an approximately 2 to 10% strength solution of, for example, calcium and/or magnesium chloride, and the dialysis is continued until the product in the tube has a calcium and/or magnesium content of about 2 to 10% by weight. The content is checked by analysis of a small portion of the product. This second dialysis is, as a rule, also carried out at room temperature, and there is counterflow of the outside liquid in this case too, advantageously for 12 to 72 hours.

However, if desired, it is possible to replace the second dialysis by direct reaction with a calcium and/or magnesium salt. The adjustment of the calcium and/or magnesium content to the desired figure is carried out with the solution itself, or with the solution which has been concentrated to a small volume, or with a dry product which has been obtained by alcohol precipitation or freeze-drying. When a solid product has been obtained, it is first dissolved in demineralized water, which is facilitated by stirring and gentle heating. The aqueous solution is then treated with an aqueous solution, for example 10% strength, of a calcium or magnesium salt; particularly suitable for this purpose are solutions of calcium chloride or magnesium chloride. Preferably, in order to promote the reaction, stirring is carried out for some time.

The resulting complex is isolated as the solid substance by concentration of the solution to a small volume and precipitation by an alcohol which is miscible with water, for example methanol or ethanol; the mixture can be left to stand for one or two hours to improve the formation of the precipitate. The precipitate is then filtered off, washed with the same or a similar alcohol, and dried under atmospheric pressure at slightly elevated temperature, to about 40° C.

Thereafter, the physicochemical properties of the resulting complex were determined as follows.

The molecular weight of the phytohemagglutinins is 15,000 to 75,000 Dalton according to the determination by gel electrophoresis.

The molecular weight distribution of the polyheteroglycan content was determined by the method of Chem. Pharm. Bull. 19, 1214–1217 (1971) using sepharose ® Cl 6 as molecular sieve. In FIG. 1 which is attached, the individual fractions with the respective molecular weights are plotted on the abscissa, while the ordinate shows the amounts of substances in each of the fractions measured by extinction. As is evident from FIG. 1, the product is composed of at least 50% of compounds having a molecular weight above 1,000,000 Dalton, of 25 to 35% of those having a molecular weight of 1,000,000 to 100,000, while compounds having a molecular weight below 10,000 represent 12% at the most.

Figure 2:
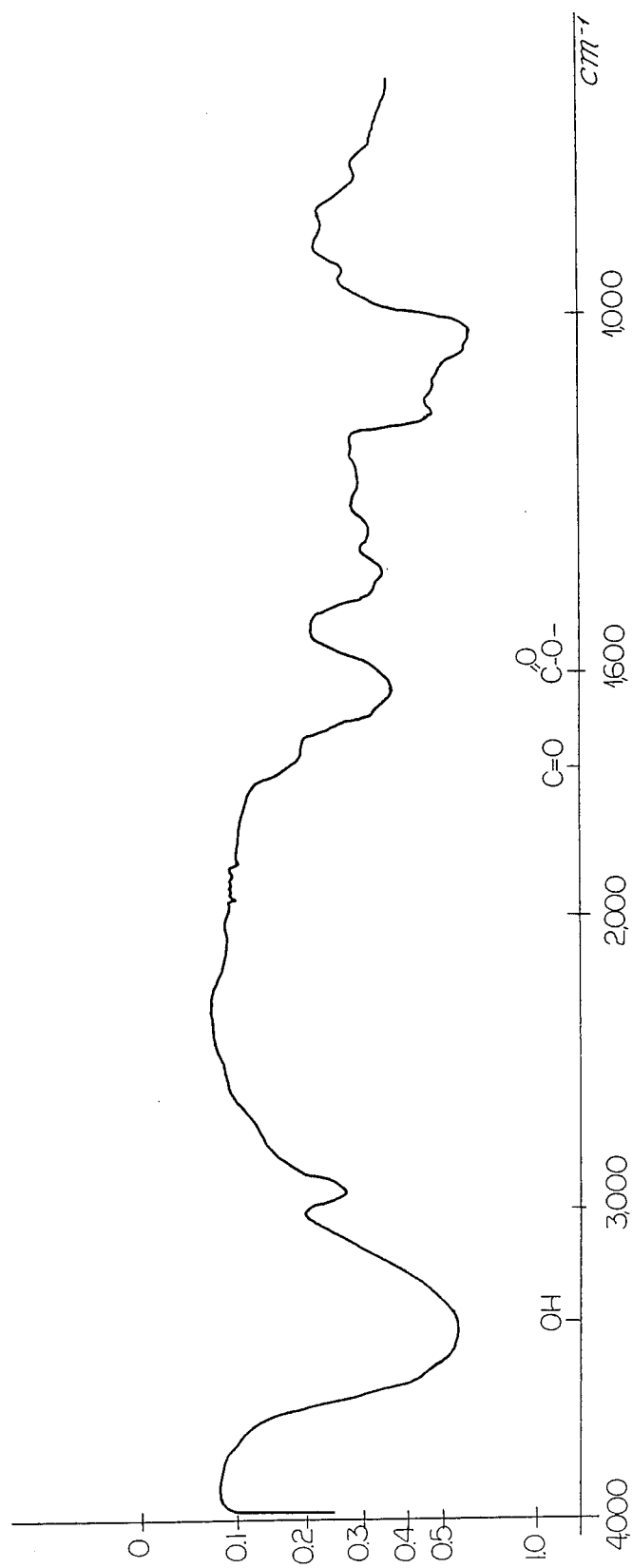

The infrared spectrum was recorded in a KBr disk with a Perkin-Elmer 257 spectrophotometer; as is evident from FIG. 2 there are broad bands at 3,400 cm$^{-1}$ and 1,750 cm$^{-1}$ and a narrow band at 1,600 cm$^{-1}$, which are assigned to a hydroxyl and a carbonyl group and to a carboxyl group respectively.

The ultraviolet spectrum was recorded for a concentration of 0.01% in water with a Unicam SP 1800 spectrometer; however, nothing characteristics is seen.

The following features emerged from detailed chemical investigation of the product.

The content of calcium and/or magnesium is 2.0 to 10% by weight, and that of phosphorus is 0.2 to 2% by weight, as determined by atomic absorption.

About 40 to 60% of the product is composed of glycans; determination was carried out by the thin-layer/gas chromatography method of Chem. Pharm. Bull. 25, 2910–2916 (1977).

The product contains monosaccharides, at least 50% of these consisting of galactose and glucose in the ratio of 1:1 and 10% of uronic acids; the determination was carried out after hydrolysis, by means of thin-layer chromatography and gas chromatography of volatile derivatives.

Elemental analysis produces the following figures:
C=35 to 45%
H=4 to 7%.
N=at least 5%

The residue on ignition or ash is not less than 15% after combustion at 600° C. for 2 hours. After the combustion, the ash has the following composition:
Potassium: 15 to 25%
Sodium: 0.1 to 2%
Calcium: 20 to 45% and/or
Magnesium: 5 to 15%

Phosphorus: 3 to 6% as determined by atomic absorption.

The peptide content is between 6 and 30%, when determined by the biuret reaction.

After acid hydrolysis, for example with hydrochloric acid, the amino acids detectable in the product lead to the conclusion that the peptide content (phytohemagglutinins) is 3 to 25% on determination in a Beckmann Biochrom 2000 amino acid analyzer.

At least 75% of the peptide content is composed of the following amino acids: aspartic acid or asparagine, glutamic acid or glutamine, alanine, glycine, lysine, serine, valine and leucine.

The molar ratio of the above amino acids is, with a range of ±25%: 4:3:2:2:2:2:1:1.

The ratio of the acid and of the basic amino acids is greater than 3:1.

The ratio of the peptide content and of the glycan content is about 1:10.

Pharmacological investigation of the new complexes was particularly directed at cytoprotective and antiinflammatory properties as well as at the acute toxicity.

The acute toxicity as determined with mice and rats afforded the following $LD_{50}$ values mouse, per os: >2,700 mg/kg rat, per os: >2,200 mg/kg mouse, intravenously: about 340 mg/kg rat, intravenously: about 280 mg/kg the compounds thus being essentially not toxic.

The cytoprotective action was tested by the alcohol ulcer test of A. J. E. Robert and coworkers, Am. J. Physiol. 245/Gastrointest. Liver Physiol. 8, G113–G121 (1983). Usually, Wistar rats in groups with 10 animals in each are kept without food for 1 day and then treated once through a stomach tube with 1 to 2 ml of anhydrous ethanol which contains 0.5% hydrochloric acid. A few hours earlier, the complex which is to be tested (prepared as in Example 3) is administered orally by stomach tube.

After the death of the animals, the length of the resulting ulcers and the size of the resulting mucosal edema in the stomach are measured and compared with control animals not treated with the product. A basic aluminum complex of sucrose polysulfate (sucralfate, see below) was used for comparison.

| Number of animals | Type of treatment | Oral dose in mg/kg | Inhibition in % | |
|---|---|---|---|---|
| | | | Edema | Ulcer |
| 10 | Control | | | |
| 10 | Complex | 50 | 52 | 24 |
| 10 | Complex | 400 | 71 | 54 |
| 10 | Sucralfate | 500 | 79 | 56 |

The antiinflammatory action was determined by means of the edema induced by carrageen in the rat paw [C. A. Winter, Proc. Soc. exp. Biol. Med. 111, 544–547 (1962)]. The complex from Example 3 is administered intraperitoneally, in parallel experiments, to groups each of six female rats of the CFY strain, with the dose increasing from one to the next. The carrageen treatment of the left rear paw is carried out 5 hours thereafter. The extent of the swelling which occurs is determined by comparison with the untreated right rear paw, and the inhibition is determined by comparison with the control group which has not been treated with the complex beforehand. The comparison product used was indomethacin. The antiinflammatory action is expressed as percentage inhibition of swelling in the Table which follows.

| i.p. doses in mg/kg | Inhibition in % |
|---|---|
| 0.5 | 23 |
| 1.0 | 25 |
| 5.0 | 48 |
| 10 | 52 |
| Indomethacin, 10 mg/kg oral | 46 |

The new complexes are distinguished on use in humans by general cytoprotective (antiulcerative) actions. In clinical investigations on patients with peptic ulcer (gastric ulcer, duodenal ulcer) or esophagitis, treatment with the complex of the invention by the orgal route showed an impressive improvement in the condition. Moreover, cases of serious varicose ulcer (leg ulcer) have been successfully treated by topical application of a gel containing the complex.

Furthermore, the complex provides to be generally active against inflammatory processes in the human body. A significant improvement was found in subjects suffering from chronic arthritis on treatment with the complex in the form of suppositories. The antiinflammatory efficacy has likewise been observed in cases of prostatitiS, dermatitis and conjunctivitis and with inflammations in the oral cavity.

The immunoregulating and especially immunostimulating properties of the complex deserve further, particular interest. They can be advntageously be applied in conditions where the resistance of the body is lowered, especially since the minimal toxicity of the complex allows the long-term treatment, which is usually necessary in such cases, without problems.

Antiviral effects, finally, are equally noteworthy. They can be observed, for instance, with diseases of the herpes group and with other viral infections too, and they may help or bring about the healing process in the relevant indications.

Quite generally, the posology in respect of oral administration is of from 0.1 to 50 mg/kg body weight for adults; a dose of from 20 to 200 mg usually is administered per os three times a day. For intravenous administration, the dose may be of from 10 to 200 mg.

However, certain metal complexes of carbohydrates had already been disclosed, especially basic aluminum complexes of disaccharide polysulfates having a sulfur content of 7 to 13% and an aluminum content of 11 to 24% [The Merck Index 1983, 1273, No. 8755; French Pat. No. 1,500,571; U.S. Pat. No. 3,432,489]. They exert an inhibitory action on gastric ulcers (peptic ulcer); the sucrose polysulfate complex is commercially available under the names Sulcralfate, Antepsin, Ulcerban, etc. The preparation is carried out by esterification of sucrose, lactose or maltose with sulfuric acid or chlorosulfonic acid, neutralization of the sulfuric acid hemiester with an alkali, and reaction of the alkali metal salt with an aluminum salt.

On the other hand, polysaccharides of widely varying composition had also already been extracted from plants. For example, nitrogen-free polysaccharides of molecular weight 5,000 to 50,000 have been isolated from plants of the family Compositae, such as Echinacea purpurea and angustifolia, by extraction with an aqueous alkali solution [Chem. Abstr. 97 (1982), 44198 c; Ztschr. für angew. Phytotherapie 2 (1981), 166; German Offenlegungsschrift No. 3,042,491]. These are pure polysaccharides composed of arabinogalactans, arabinoglucans and arabinoxylans; they have immunostimulating properties and, at the same time, an antiinflammatory action. The calcium and magnesium complexes according to the invention differ essentially from the latter compounds, either by their composition (phosphorus and peptide component) or by their molecular weight.

A polysaccharide of approximate molecular weight 8,000 and specific rotation $[\alpha]_D^{22} = +16.7°$ (water) is obtained from the bark of Melia asadirachta by extraction with hot water and filtration through molulcar sieves (Japanese Published Specification No. 57-105,533). The sugar constituents are glucose, arabinose and fucose in the ratio 6:1:1; the polysaccharide has an antiinflammatory action. The new complexes differ unambiguously from the latter, either by the composition itself (alkaline earth metal, phosphorus, peptide component). or by the molecular weight and the lack of optical activity.

A homogeneous product of molecular weight 1,800,000 and specific rotation $[\alpha]_D^{18} = +61.6°$ (in 0.1% NH4OH) has been isolated from the leaves of Althea officinalis [Chem. Pharm. Bull. 29 (1981), 2277–2282], but with no data on pharmacological properties or possible uses. It is composed mainly of a partially acetylated acid polysaccharide in addition to 3.3% amino acids: the polysaccharide itself is composed of L-rhamnose, D-galacturonic acid and D-glucuronic acid. The product according to the invention differs from the latter, inter alia, by the complex-bound calcium and/or magnesium, by the phosphorus content and by the absence of optical activity.

A polysaccharide concentrate of molecular weight 75,000 to 2,000,000 has been obtained from plants such as camomile and lime-tree flowers (Chamomillae and Tiliae flos), mallow and plantago species, Trigonella foeni graeci, Cucurbita maxima and Kitaibela vitifolia (European Patent Publication No. 89,529). It is characterized especially by a nitrogen content of at most 5% and a glycan content of at least 60% comprising the sugars glucose, galactose, xylose, rhamnose and arabinose as well as uronic acids, and has antiinflammatory actions. The new complexes clearly differ therefrom, beside the calcium and/or magnesium content, by inter alia their nitrogen and glycan content of at least 5% and at most 60%. respectively, and by their pharmacological spectrum of activity.

Finally, it is worth mentioning a glycoprotein called aloctin A which has been isolated from plants of the genus Aloe (Japanese Published Specification No. 54-73,109). The compound is distinguished by, inter alia, antitumor and antiinflammatory properties. It has a molecular weight of the order of magnitude of 18,000 and a ratio by weight of the protein to the sugar component of 8:2. This ratio alone demonstrates the difference from the calcium and magnesium complexes according to the invention, in which the ratio of the pepetide and of the glycan content is about 1:10.

The invention is illustrated in detail by means of the Examples which follow.

EXAMPLE 1

560 ml of KH2PO4/Na2HPO4 buffer solution of pH 8.5 are added to 1.0 kg of the aerial part of freshly harvested Tussilago farfara (Compositae) with a dry matter content of 20%, the mixture is ground to a paste and agitated in a kneading machine at 40° C. for 3 hours and then centrifuged. The sediment is suspended in 300 ml of buffer solution of pH 8.5 and, after agitating for ½ hour, is centrifuged. The liquid is carefully pressed out of the sediment and combined with the filtrate. The mixture is left to stand for 4 hours for a precipitate to settle out and is filtered through a Seitz K5 filter (manufacturer: Seitz-Werke GmbH, 6550 Bad Kreuznach, FRG). 1,450 ml of clear filtrate are obtained in this way. 4,350 ml of 96% pure ethanol are added to the vigorously stirred filtrate, and the mixture is left to stand at room temperature for 8 hours. The aqueous mother liquor is removed from the precipitate by decantation, and the residue is taken up in 100 ml of demineralized water and freeze-dried. The yield is 20.0 g of crude complex.

Peptide content: 15% (by the biuret reaction)
Glycan content: 52% (determination by gas chromatography after hydrolysis)
Ash: 24% (after heating at 600° C. for 2 hours)
Calcium: 3.6% (determination by atomic absorption spectroscopy)
Biological activity: 50% (carrageen rat paw test).

EXAMPLE 2

First the process of Example 1 is carried out.

20 g of the resulting crude complex are dissolved in 400 ml of water, and concentrated ammonium hydroxide is added to the solution until the pH reaches 9.0. The mixture is stirred at 40° C. for 3 hours and an insoluble residue is removed by centrifugation. 160 g of ammonium sulfate are added to the clear solution, with stirring, and the mixture is left to stand at 25° C. for 12 hours until the precipitate has settled out. The resulting precipitate is removed by centrifugation, and water is removed by trituration with 100 ml of acetone. The weight of the acetone-moist lectin fraction is 3.0 g. The product is dissolved in 10 ml of 8% strength aqueous ammonium solution, and the solution is dialyzed against running demineralized water in a standard dialysis tube from Kalle for 12 hours.

During the dialysis, the content of inorganic salts in the product decreases to 3.0%, which can be checked by quantitative analysis of the ash on a small portion of the product. After the said concentration of inorganic salts has been reached, the running water on the outside is replaced by an aqueous 10% strength calcium chloride solution, and the dialysis is continued for 12 hours. The final product is then freeze-dried. The yield is 0.50 g of purified complex, whose characteristic features on determination by the methods indicated in Example 1 are the following:

Peptide content: 30%
Glycan content: 55%
Ash: 17%
Calcium: 8%
Biological activity: 66%.

EXAMPLE 3

850 ml of phosphate buffer solution of pH 8.5 are added to 1.0 kg of fruits of Cucurbita pepo convar. Styriaca with a dry matter content Of 12%, the mixture is ground to a paste and is treated in a kneading machine at 30° C. for 2 hours, and then filtered through a pressure filter under 10 atmospheres gauge pressure. The residue is stirred in 400 ml of phosphate buffer solution and is centrifuged. The filtrates are combined and filtered through a Seitz K5 filter under vacuum. This results in 2,000 ml of clear filtrate. 9.0 liters of 96% pure ethanol are added to the vigorously stirred filtrate at 40° C., and the mixture is cooled to 20° C. and left to stand for 12 hours. The resulting precipitate is removed by centrifugation, and the moist precipitate is washed twice with 200 ml of 96% pure ethanol and, without allowing to dry, is dissolved in 400 ml of water; the pH of the solution is brought to 9.0 by addition of concentrated ammonium hydroxide. After the mixture has been stirred continuously for 3 hours, it is centrifuged, and the supernatant liquid is removed and mixed, with stirring, with 120 g of ammonium sulfate and left to stand at 30° C. for 8 hours.

The resulting precipitate is removed by centrifugation and washed with 100 ml of 96% pure ethanol. The material, which weights approximately 2.4 g and is somewhat moist, is dissolved in 12 ml of 4% strength ammonium hydroxide solution, and the solution is dialyzed against running demineralized water in a standard dialysis tube from Kalle for 24 hours. Subsequently, the water flowing on the outside is replaced by a 6% strength calcium chloride solution, and the dialysis is continued for a further 48 hours. 36 ml of methanol are added to the solution in the dialysis tube and, afrter having been left to stand for 4 hours, the precipitate is isolated by vacuum filtration, washed with methanol and dried in the air at 40° C.

Yield: 0.40 g of complex, whose characteristic features on determination by the methods indicated in Example 1 are the following: Peptide content: 28%, Glycan content: 58%, Ash: 17%, Calcium: 4.5%, Biological activity: 65%.

EXAMPLE 4

1.0 kg of the aerial part of Althea officinalis (Malvaceae) is treated by the process of Example 1.

Yield: 32.0 g of crude complex, whose characteristic features on determination by the methods indicated in Example 1 are the following: Peptide content: 10.5%, Glycan content: 42%, Ash: 17%, Calcium: 2.5%, Biological activity: 44%

EXAMPLE 5

1.0 kg of the aerial part of freshly harvested Tussilago farfara (Compositae) is ground and extracted with 0.9 liter of sodium chloride solution of a concentration of 0.15 mole/liter and of pH 8.2, with stirring, at 40° C. for 2 hours. The solid residue is removed by filtration and is reextracted with 0.6 liter of sodium chloride solution. The two extracts are combined, 4.5 liters of methanol are added at 40° C., with stirring, and, after being left to stand for 12 hours, the precipitate is removed by filtration. It is dissolved and dialyzed as in Example 2, but in place of the second dialysis 15 ml of 10% strength magnesium chloride solution are added to the solution in the dialysis tube. Thereafter the lectin complex is precipitated by addition of 90 ml of 96% pure ethanol. The precipitate is removed by filtration, washed with ethanol and dried in vacuo.

The yield is 0.60 g of purified complex, whose characteristic features on determination by the methods indicated in Example 1 are the following:

Peptide content: 25%
Glycan content: 55%
Ash: 15%
Magnesium: 4.6%
Biological activity: 57%

EXAMPLE 6

200 g of wheat germ (Triticum vulgare, Gramineae) are ground, and the paste is extracted with 7,000 ml of water of pH 8.0, which contains 10% by volume of methanol, and the mixture is left to stand at 40° C. for 3 hours. It is filtered through a pressure filter, and the filtrate is purified by centrifugation and vacuum filtration and is subsequently concentrated to a volume of 500 ml under reduced pressure. 1,500 ml of 96% pure ethanol are added to the resulting concentrate at 20° C., and the resulting precipitate is removed by centrifugation. The slightly gummy precipitate is taken up in 30 ml of distilled water and freeze-dried.

The yield is 11.0 g of crude complex, whose characteristic features on determination by the methods indicated in Example 1 are the following:

Peptide content: 18%
Glycan content: 47%
Ash: 24%
Calcium: 2.8%
Biological activity: 43%

The following experiments serve further to identify and elucidate the structure of the new complexes.

(a) 20 g of the crude complex prepared by the process of Example 1 (with a peptide content of 15% and a biological activity of 50%) are dissolved in 600 ml of water in which 750 g of galactose have previously been dissolved. The solution is stirred at 40° C. for 3 hours and then centrifuged; the supernatant liquid is removed and mixed with 2,000 ml of ethanol. The precipitate is removed by filtration and dried. 10.5 g of polyheteroglycan-rich product with the following features are obtained:

Peptide content: 3.1%
Biological activity: 16%.

The residue which is insoluble in the aqueous galactose solution and has been removed by centrifugation is washed with a 1:1 (vol/vol) ethanol/water mixture and dried under reduced pressure at 40° C. 3.0 g are obtained.

Peptide content: 18.5%
Biological activity: 57%.

(b) 10 g of the crude complex prepared by the process of Example 1 (with a peptide content of 15% and a biological activity of 50%) are dissolved in 300 ml of water which has been adjusted to pH 9.0 with sodium hydroxide solution, and the insoluble part is removed by filtration. 100 ml of an aqueous solution in which 0.1 g of protease (alkaline protease, manufacturer: Sigma Chemical Co., St. Louis, Mo./USA) has been dissolved at pH 9.0 are added to the solution; the solution is now agitated at 40° C. for 12 hours. It is then centrifuged, and the supernatant liquid is removed and mixed with 160 ml of ethanol. The mixture is centrifuged, and the precipitate is dissolved in 20 ml of water and freeze-dried. 3.6 g are obtained.

Peptide content: 2.7%
Biological activity: 17%.

(c) Relation between the biological activity and the peptide content of the crude complex prepared by the process of Example 3.

| Peptide content % | Biological activity % |
| --- | --- |
| 23.7 | 69 |
| 20.3 | 61 |
| 16.5 | 52 |

| Peptide content % | Biological activity % |
| --- | --- |
| 11.0 | 46 |
| 8.6 | 34 |

(d) Relation between the calcium content and the biological activity of the complex.

10.0 g of the crude complex prepared by the process of Example 1 (with a calcium content of 3.6% and a biological activity of 50%) are dissolved in 500 ml of distilled water, the solution is adjusted to pH 3.5 with acetic acid, and 100 ml of 2.5% strength ammonium oxalate are added. The resulting precipitate is removed by filtration, and the clear solution is dialyzed in a standard dialysis tube from Kalle against demineralized water until it is free of oxalate. The resulting solution is divided into two.

One part is dialyzed against an 8.0% strength calcium chloride solution for 24 hours. After the dialysis is complete, 900 ml of ethanol are added to the solution, and the precipitate is removed by filtration and dried. 3.8 g are obtained.

Calcium content: 4.5%
Biological activity: 51%.

900 ml of 96% pure ethanol are added to the second part which has not been dialyzed, and the precipitate is removed by filtration and dried. 3.3 g are obtained.

Calcium content: 0.3%
Biological activity: 16%.

(e) Preparation of the lectin-rich and lectin-poor complexes.

100 g of the crude complex prepared by the process of Example 1 (with a peptide/glycan ratio of 1:2 and a biological activity of 47%) are dissolved in 3,000 ml of water at 40° C., whose pH has been brought to 9.5 by addition of concentrated ammonium hydroxide, the solution is stirred for 6 hours, and the residue is removed by filtration. 2,880 ml of clear solution are obtained. 1,152 g of ammonium sulfate are added to the stirred solution, and the solution is left to stand until the next day to allow the precipitate to settle out.

The precipitate is removed by centrifugation, washed with ethanol and dried.

The following are obtained: 26.0 g of precipitate, 2,860 ml of clear solution.

The precipitate is dissolved in 500 ml of water, and the solution is dialyzed against tap water for 24 hours; 1,500 ml of ethanol are then added to the solution, and the precipitate is removed by filtration and dried. 4.7 g are obtained; the precipitate thus obtained is rich in lectins.

Peptide/glycan ratio=2:1
Biological activity: 69%.

The clear solution is dialyzed as above, and is concentrated to a volume of 320 ml under reduced pressure. 960 ml of 96% pure ethanol are added to this solution, and the precipitate is removed by filtration and dried. 60 g are obtained; the precipitate which is thus obtained is poor in lectins.

Peptide/glycan ratio=1:3
Biological activity: 32%.

EXAMPLE 7

1.0 kg of wheat bran the main part of which consists of the pericarp, the spermoderm and the perisderm of Triticum vulgare seu sativum, with a maximal particle size of 2 mm, is thoroughly mixed with 2.4 liter of water of pH 8.0 and 20° C. in which 48 1 g of sodium chloride are dissolved. The resulting slurry is slowly stirred for 10 hours and then squeezed out by means of a hydraulic press. The liquid part amounts to 2150 ml; it is centrifuged at 4,000 r.p.m. for 30 minutes. There are obtained 150 g of sediment and 2000 ml of supernatant. Separation is carried out by decantation and the supernatant is filtered through Seitz K5 filter.

The filtrate is concentrated to a volume of 300 ml at 45° C. and a pressure of 90 Torr. 900 ml of 96% pure ethanol are added to the vigorously stirred concentrate. A precipitate is formed and is left to stand at 20° C. for 24 hours. The precipitate is isolated by filtration, suspended twice, each time in 50 ml of 96% pure ethanol, isolated by filtration and again washed with 50 ml of 96% pure ethanol. It is eventually dried at 45° C. and normal pressure.

Yield: 55 g of complex whose characteristic features are the following: Infrared spectrum: broad bands at 3,400 and 1,750 cm$^{-1}$ Peptid content: 15.2% (determined by the biuret reaction), Glycan content: 51% (the whole sugars), Ash: 22.9 (after combustion at 600° C. for 2 hours), Calcium and magnesium: 4.5%, Biological activity: 40% inhibition in female rats at i.p. dose of 10 mg/kg (carrageen rat paw test of Winter), 50% inhibition in female rats at oral dose of 400 mg/kg (alcohol ulcus test of Robert)

EXAMPLE 8

A slurry is prepared from 55 g of the crude complex as obtained according to Example 7 and 500 ml water of 20° C. by stirring for 3 hours in a mixer and the slurry is centrifuged at once. The supernatant which consists of 450 ml of a liquid is shaked with 450 ml of n-butanol and left to stand. The butanol phase is of a brownish-yellow colour; the complex lies as a precipitate under the liquid phase. It is again centrifuged in order that the butanol be completely removed.

750 ml of ethanol are added to the precipitate and the whole mixture is left to stand at room temperature for 24 hours. It is then filtered and the precipitate is suspended three times, each time in 40 ml of 96% pure ethanol, filtered and dried.

Yield: 43 g of a complex of a beige colour whose characteristic features are the following: Infrared spectrum: broad bands at 3400 and 1750 cm$^{-1}$ Peptide content: 18,6% (determined by the biuret reaction), Glycan content: 60% (the whole sugars), Ash: 17,1% (after combustion at 600° C. for 2 hours), Calcium and magnesium: 2,5%, Biological activity: 60% inhibition in female rats at i.p. dose of 10 mg/kg (carrageen rat paw test of Winter), 65% inhibition in female rats at oral dose of 400 mg/kg (alcohol ulcus test of Robert)

EXAMPLE 9

The starting material consists of 300 ml of a concentrate which was prepared according to Example 7. The thus obtained concentrate is dissolved in an aqueous solution of 50 g of urea and 15 g of finely ground calcium chloride. To the thus obtained solution, 800 ml of 96% pure ethanol are slowly added with vigorous stirring and the mixture is left to stand for 24 hours. The precipitate then is isolated by filtration and washed three times, each time with 30 ml of 96% pure ethanol. After filtration, the product is dried at a temperature of at most 45° C.

Yield: 45 g of a complex of a beige colour whose characteristic features are the following: Infrared spectrum: broad bands at 3400 and 1750 cm$^{-1}$. Peptid content: 14,6% (determined by the biuret reaction), Glycan content: 55% (the whole sugars), Ash: 19,6% (after combustion at 600° C. for 2 hours), Calcium and magnesium: 3,6%, Biological activity: 50% inhibition in female rats at i.p. dose of 10 mg/kg (carrageen rat paw test of Winter), 58% inhibition in female rats at oral dose of 400 mg/kg (alcohol ulcus test of Robert). F

I claim:

1. Calcium and magnesium complexes of phytohemagglutinin-polyheteroglycans of plant origin with antiinflammatory, immunostimulating and cytoprotective action, comprising:

a molecular weight of the phytohemagglutinins between 10,000 and 75,000 Dalton (determined by gel electrophoresis), an infrared spectrum as shown in FIG. 2, with broad band at 3,400 and 1,750 cm$^{-1}$ and a narrow band at 1,600 cm$^{-1}$, a content of calcium and/or magnesium of 2.0 to 10.0% a phosphorus content of 0.2 to 2% a content of glycans of 40 to 60%, including monosaccharides which are composed of at least 50% galactose and glucose in the ratio of 1:1 and of 10% uronic acids, an elemental analysis of 35 to 45% carbon, 4 to 7% hydrogen and at least 5% nitrogen, after combustion, an ash of the following composition: 15 to 25% potassium, 0.1 to 2.0% sodium, 20 to 45% calcium and/or 5 to 15% magnesium, and 3 to 6% phosphorus, a residue on combustion of at least 15% (600° C., 2 hours), a peptide content (phytohemagglutinins) of 3 to 25% (determined by amino acid analysis), a peptide content of 6 to 30% (determined by the biuret reaction), a peptide content which is composed of at least 75% of the following amino acids: aspartic acid or asparagine, glutamic acid or glutamine, alanine, glycine, lysine, serine, valine and leucine, a ratio for the acid and of the basic amino acids of at least 3:1, a molecular ratio of the peptide content and of the glycan content of 1:10, and a cytoprotective action at the oral dose of 400 mg/kg of at least 40% in the rat (determined by the Robert alcohol ulcer test).

2. Calcium and magnesium complexes as claimed in claim 1, wherein the phytohemagglutinin-polyheteroglycan portion is derived from one or more plants selected from the group consisting of the following families: Compositae, Malvaceae, Cucurbitaceae and Gramineae.

3. Calcium and magnesium complexes as claimed in claim 2 wherein the phytohemagglutinin-polyheteroglycan portion is derived from a plant selected from the group consisting of Tussilago farfara, Althea officinalis, Cucurbita pepo convar. Styriaca and Triticum vulgare.

4. A process for the preparation of the calcium and magnesium complexes as claimed in claim 1, which comprises comminution of a plant, or a part thereof, containing a phytohemagglutinin-polyheteroglycan, extraction of the plant material with a buffer solution of pH 8 to 9, removal of the aqueous extract from the solid plant residue, precipitation of the phytohemagglutinin-polyheteroglycan complex from the extract by treatment thereof with an alcohol which is miscible with water, said alcohol being added in a volume which is a multiple of the volume of the extract, removal of the precipitate from the liquid and adjusting the calcium and/or magnesium content of the complex to the desired amount of 2.0 to 10.0% by weight.

5. The process as claimed in claim 4, wherein the plants or parts of plants which contain phytohemagglutinin-polyheteroglycans and are used are selected from the group consisting of the family Compositae, Malvaceae, Cucurbitaceae or Gramineae.

6. The process as claimed in claim 4, wherein the extraction is carried out with an aqueous sodium chloride solution of a concentration of up to 0.2 mole/liter and a pH value of 8 to 9.

7. The process as claimed in claim 4, wherein the extraction is carried out with a buffer solution of pH 8 to 9, containing 10 to 20% by volume of methanol or ethanol.

8. The process as claimed in claim 4, wherein, for the precipitation of the complex, the extract is brought to an alcohol content of 75 to 95% by volume by addition of methanol or ethanol.

9. The process as claimed in claim 4, wherein the phytohemagglutinin-polyheteroglycan complex resulting from the treatment of the extract with alcohol is further purified by dissolution in a buffer solution of pH 8 to 9, removal of insolubles, and precipitation from the solution by addition of ammonium sulfate, before removal of the precipitate from the liquid and adjusting the calcium and/or magnesium content.

10. The process as claimed in claim 4, wherein the resulting complex is adjusted to a calcium and/or magnesium content of 2 to 10% by weight by dissolution in weakly alkaline solution and dialysis of the solution against an aqueous solution of a calcium or magnesium salt.

11. The process as claimed in claim 4, wherein the resulting complex is adjusted to a calcium and/or magnesium content of 2 to 10% by weight by dissolution in weakly alkaline solution, dialysis of the solution against demineralized water, and addition of an aqueous solution of a calcium or magnesium salt.

12. Pharmaceutical formulations which comprise as active compound the calcium or magnesium complexes as claimed in claim 1, and their pharmaceutically acceptable excipients, vehicles or diluents.

13. A method for the therapeutic treatment of ulcers in any location or of inflammations, which comprises administering to a patient in need thereof an effective amount of the calcium and/or magnesium complexes as claimed in claim 1.

14. A method for the therapeutic treatment of gastric ulcers duodenal ulcers and esophagitis comprising administering to a patient in need of such treatment an effective amount of the pharmaceutical formulation of claim 12.

15. A process, as in claim 4 wherein the alcohol is added in a 30–40 fold volume relative to the weight of the plant material used.

* * * * *